United States Patent
Gleich et al.

(10) Patent No.: US 7,482,807 B2
(45) Date of Patent: Jan. 27, 2009

(54) METHOD OF DETERMINING A SPATIAL DISTRIBUTION OF MAGNETIC PARTICLES

(75) Inventors: Bernhard Gleich, Hamburg (DE); Juergen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 126 days.

(21) Appl. No.: 11/575,574

(22) PCT Filed: Sep. 20, 2005

(86) PCT No.: PCT/IB2005/053088

§ 371 (c)(1),
(2), (4) Date: Mar. 20, 2007

(87) PCT Pub. No.: WO2006/035359

PCT Pub. Date: Apr. 6, 2006

(65) Prior Publication Data

US 2008/0204009 A1    Aug. 28, 2008

(30) Foreign Application Priority Data

Sep. 28, 2004  (EP) .................................. 04104731

(51) Int. Cl.
*G01V 3/00* (2006.01)

(52) U.S. Cl. ...................................... 324/309; 324/319
(58) Field of Classification Search ......... 324/300–322; 600/407–422
See application file for complete search history.

(56) References Cited

U.S. PATENT DOCUMENTS 6,470,220 B1 * 10/2002 Kraus et al. ................. 607/103
7,300,452 B2 * 11/2007 Gleich ......................... 607/105

FOREIGN PATENT DOCUMENTS

DE    10151778    5/2003
WO    2004018039   3/2004

OTHER PUBLICATIONS

B. Gleich and J. Weizenecker; "Tomographic Imaging Imaging Using the Nonlinear Response of Magnetice Particles", Nature, vol. 435, No. 7046, pp. 1214-1217, 2005, XP002368326.
Romanus E et al; "Magnetic Nanoparticle Relaxation Measurement as a Novel Tool Fro In Vivo Diagnostics", Journal of Magnetism and Magnetic Materials, Elsevier, Amsterdam, NL, vol. 252, pp. 387-389, 2002, XP004395246.
Talmadge J M et al; "Magneto-Optical Detection of Weak Magnetic Fields", Biomedical Imaging Macro to Nano, IEEE International Symposium, Arlington, VA, pp. 1514-1515, Apr. 15, 2004, XP010774155.

* cited by examiner

Primary Examiner—Brij B Shrivastav (57) ABSTRACT

The invention relates to a method of determining a spatial distribution of magnetic particles in an examination zone, in which method a first magnetic field is generated, which forms in the examination zone a first sub-zone having a relatively low magnetic field strength and a second sub-zone having a relatively high magnetic field strength. The position in space of the two sub-zones is then changed by a second magnetic field, whereby the magnetization in the examination zone is changed. Signals dependent on the change in magnetization are acquired and evaluated to extract information concerning the spatial distribution of the magnetic particles. The second magnetic field is generated so that the time derivative of the second magnetic field is substantially identical for each spatial component.

12 Claims, 7 Drawing Sheets

METHOD OF DETERMINING A SPATIAL DISTRIBUTION OF MAGNETIC PARTICLES

The invention relates to a method of determining a spatial distribution of magnetic particles in an examination zone. Furthermore, the invention relates to an apparatus for implementing the method according to the invention and to a computer program for controlling the apparatus according to the invention.

A method of the kind mentioned at the beginning is known from DE 101 51 778. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed.

The disadvantage of this known method is that the quality of the resulting image of the examination zone is often not satisfactory, for example, for the purposes of medical diagnostics.

It is therefore an object of the present invention to specify a method of the kind mentioned initially, in which the quality of the image formed is improved.

That object is achieved by a method of determining a spatial distribution of magnetic particles in an examination zone with a first, time-constant magnetic field and a second, time-variable magnetic field, wherein the second, time-variable magnetic field has a fundamental frequency and an amplitude in each spatial component and the time derivative of the second magnetic field is substantially identical for each spatial component, or the second, time-variable magnetic field encompasses a sum of several second, time-variable partial magnetic fields, each partial magnetic field having a fundamental frequency and an amplitude in each spatial component and the time derivative of the second magnetic field and/or of the second partial magnetic fields being substantially identical for each spatial component.

When the speed at which the first sub-zone moves in the examination zone is substantially identical in all directions in space, then the resolution of an image that contains information concerning the spatial distribution of the magnetic particles is also substantially identical in each direction in space, whereby the quality of the resulting image is increased compared with the prior art mentioned at the beginning.

In particular, a time derivative of the second magnetic field for a spatial component is substantially identical within the scope of the invention to a time derivative of the second magnetic field for a different spatial component, when a measure of the magnitude of the time derivative for the one spatial component yields a value that is not less than one fifth and not greater than five times a value that is determined by applying this measure to the time derivative for the other spatial component. This measure of the magnitude of the time derivative is preferably the quadratic mean of the time derivative over time for the respective spatial component. Alternatively, for each spatial component the maximum of the time derivative could be used as measure.

A time derivative of the second magnetic field, which is substantially identical for all spatial components, is realized in an especially simple manner in claim 2, owing to the fact that the product of amplitude and fundamental frequency is substantially identical for each spatial component. In particular, two products are substantially identical when one product is not greater than five times or less than one fifth of the other product. This applies correspondingly to two frequencies that are substantially identical.

In the embodiment as claimed in claim 3, the fundamental frequencies for each spatial component of the second magnetic field are substantially identical. The effect of substantially identical fundamental frequencies for each spatial component and hence in each direction in space is that the signals acquired in step c) have a substantially identical frequency in each direction in space, the result being that the signal-to-noise ratio is substantially identical in each direction in space, which in turn improves the quality of the image that contains information concerning the spatial distribution of the magnetic particles in the examination zone.

The acquired signals, which are used to extract information, are induced in a suitable acquisition means, for example, in a coil, by changing the magnetization in the examination zone. As is generally known, the signal values of the induced signals become larger as the rate of change in the magnetization increases. In the embodiment as claimed in claim 4, a temporal Fourier transform of the second magnetic field has values in a first frequency range, which are caused by slowly changing offsets of the second magnetic field, wherein the first frequency range contains values that are smaller than each of the fundamental frequencies. That is, the fundamental frequencies are larger than the frequencies of the Fourier transform of the second magnetic field caused by the offsets. In particular, as claimed in claim 5, the fundamental frequencies are larger than ten times and preferably one hundred times the largest frequency lying in the first frequency range, with the result that the first sub-zone is quickly shifted in the examination zone. This leads to rapid magnetization changes in the examination zone and hence to large induced signal values. The second magnetic field according to the invention therefore enables induced signals having a good signal-to-noise ratio to be acquired, with the result that the quality of the information concerning the spatial distribution of the magnetic particles in the examination zone is further improved.

Furthermore, besides the rapid movement of the first sub-zone caused by the portions of the second magnetic field oscillating at the fundamental frequencies, the offsets changing slowly with time cause an additional, slow shift of the first sub-zone, with the result that a larger area of the first sub-zone can be recorded and the examination zone is enlarged. The offsets change so slowly that they make no or hardly any contribution to the signals evaluated in step d), since the signals induced by the change in the offsets are very small owing to the slow movement of the first sub-zone.

An improvement in the contrast of the image and hence in the image quality is obtained when at least one of the fundamental frequencies changes with time, as claimed in claim 6, and when in particular at least one of the fundamental frequencies increases with time.

An embodiment as claimed in claim 7 ensures that the position of the two sub-zones in the examination zone is changed in such a way that the first sub-zone approaches each point of the examination zone at least as far as a predetermined minimum distance. Thus it is possible, by suitable selection of the minimum distance, to record each point in the examination zone as the method according to the invention is being carried out.

The selection of a minimum distance as claimed in claim 8 ensures that the resolution of the method according to the invention is not reduced by a minimum distance that is too large.

The acquisition of the signals dependent on the change in the position of the sub-zones, as claimed in claim 9, by inducing signals in at least one acquisition means, especially in at least one receiving coil, is technically simple to accomplish and following evaluation of the signals provides high-quality information concerning the spatial distribution of the magnetic particles in the examination zone.

An apparatus for carrying out the method in accordance with the invention is described in claim 10. Claim 11 describes an embodiment with which a second magnetic field according to the invention can be generated especially easily. Claim 12 defines a computer program for control of an apparatus according to claim 10.

These and other aspects of the invention are apparent from and will be elucidated, by way of non-limitative example, with reference to the embodiments described hereinafter.

Figure 1:
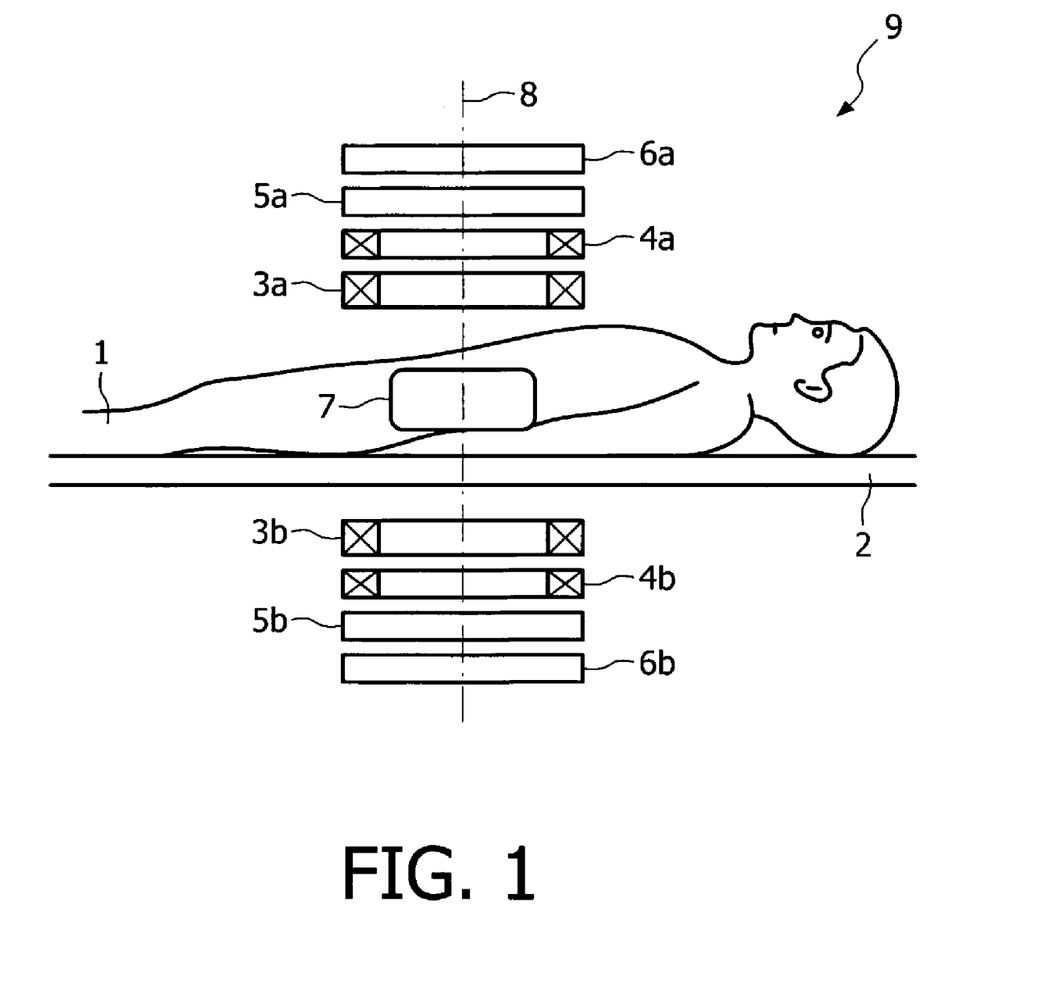
FIG. 1 shows a schematic representation of an apparatus in accordance with the invention for carrying out the method in accordance with the invention.

FIG. 1 shows an embodiment of an apparatus 9 in accordance with the invention. An object, in this case a patient 1, is arranged on a patient support table 2. Magnetic particles, which have been administered to the patient, for example, in liquid or meal form, are present in the patient, for example, in his gastrointestinal tract, and in an examination zone of the apparatus 9. The dimensions of the examination zone depend in particular, as will be explained in detail below, on the magnetic fields and magnetic particles employed.

Figure 2:
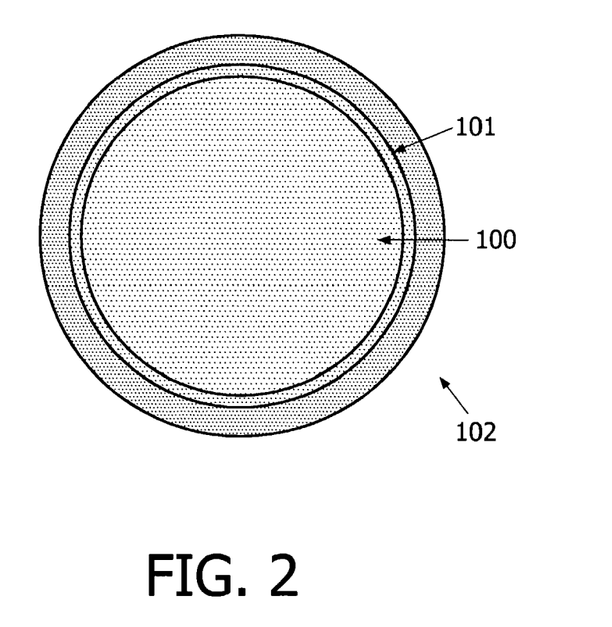
FIG. 2 shows one of the magnetic particles present in the examination zone.

A magnetic particle is illustrated in FIG. 2. It comprises a spherical substrate 100, for example, of glass, which is covered with a soft-magnetic layer 101, which has a thickness of, for example, 5 nm and consists, for example, of an iron-nickel alloy (for example, permalloy). This layer can be covered, for example, with a cover layer 102, which protects the particle against acid. The strength of the magnetic field required for the saturation of the magnetization of such particles is dependent on their diameter. In the case of a diameter of 10 µm, a magnetic field of 1 mT is required, whereas in the case of a diameter of 100 µm, a magnetic field of 100 µT is sufficient. If a coating having a saturation magnetization lower than permalloy is chosen, the magnetic field that is required for saturation is naturally further reduced.

The magnetic field strengths mentioned within the scope of the invention are specified in tesla for the sake of simplicity. This is not quite correct, as tesla is the unit of magnetic flux density. In order to obtain the particular magnetic field strength, the value specified in each case still has to be divided by the magnetic field constant $\mu_0$.

The invention is not restricted to the magnetic particles just described. On the contrary, the method in accordance with the invention can be carried out with any magnetic particle that has a non-linear magnetization curve, that is, in which the gradient of the magnetization of the magnetic particle is non-linear in dependence on a magnetic field strength acting on the particle.

What are known as monodomain particles of ferromagnetic or ferrimagnetic material can also be used. These particles have dimensions in the nanometer range and are so small that no magnetic domains or Weiss zones can form therein. These particles can be injected into the blood stream of a patient in a suitable colloidal dispersion. Such dispersions are already injected as a contrast agent in the field of magnetic resonance (MR). The magnetic particles used therein have a size of from 5 to 10 nm. This size is not the best for the method in accordance with the invention, however, since the magnetic field strength required for saturation decreases with three times the particle diameter. The magnetic particles should therefore be as large as possible, but not so large that magnetic domains are able to form. Depending on the magnetic material, the most favorable size of a magnetic monodomain particle lies at a value of between 20 and 800 nm. A material suitable for monodomain particles is, for example, magnetite ($Fe_3O_4$). Such particles can be inhaled, for example, for examination of the lungs.

Within the scope of the invention, the expression "magnetic particle" includes also particles that are magnetizable.

Figure 3:
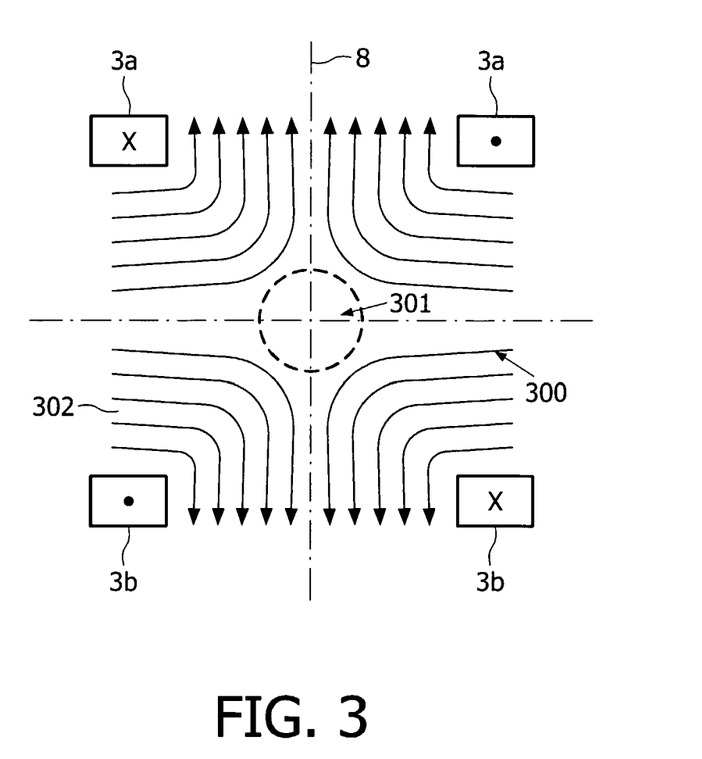
FIG. 3 shows the field line pattern of a first, time-constant magnetic field in the apparatus of FIG. 1.

Above and beneath the patient 1 there is a first pair of coils 3a, 3b (first magnetic means), which comprises two identically constructed coils 3a, 3b arranged coaxially above and beneath the patient 1 (see FIG. 1) and through which currents of identical magnitude flow, but in opposite directions; the coils generate a first, time-constant magnetic field. The first magnetic field is represented in FIG. 3 by the field lines 300. In the direction of the common coil axis 8 it has a substantially constant gradient, and at a point on this coil axis reaches a zero value. Starting from this field-free point, the magnetic field strength increases in all directions in space as the distance from this point increases. In a first sub-zone 301, which is indicated by a dashed line in FIG. 3 and is arranged around the field-free point, the magnetic field strength of the first magnetic field is so low that the magnetization of magnetic particles present therein is not saturated. In contrast, in a second sub-zone 302, which lies outside the first sub-zone 301, the magnetization of the magnetic particles is saturated.

By means of second, time-variable magnetic field, which is superimposed on the first magnetic field, the first sub-zone 301 of the first magnetic field can be shifted within the examination zone towards the field strength of the second magnetic field.

The movement and the dimensions of the first sub-zone 301, the magnetic properties and the distribution of the magnetic particles determine the size of the examination zone. Each region of the object to be examined, that is, for example, the patient 1, that contains magnetic particles of which the magnetization is changed by virtue of the position change of the first sub-zone 301, is encompassed by the examination zone.

To generate the second, time-variable magnetic field, second magnetic means are used, comprising three coil pairs. The coil pair 4a, 4b generates a magnetic field component of the second magnetic field that extends in the direction of the coil axis 8 of the first coil pair 3a, 3b. For that purpose, equal currents flowing in the same direction of rotation flow through the coils 4a, 4b. The effect that can be achieved with the coil pair 4a, 4b can in principle also be achieved by superimposing currents flowing in the same direction on the oppositely directed equal currents in the first coil pair 3a, 3b, with the result that the current decreases in the one coil pair and increases in the other coil pair.

To generate magnetic field components of the second magnetic field in directions that are oriented perpendicularly to the coil axis of the coil pair 3a, 3b, two further coil pairs 5a, 5b and 6a, 6b are used. Like the coil pairs 3a, 3b and 4a, 4b, these coil pairs 5a, 5b and 6a, 6b could be Helmholtz-type coils, but then the examination zone would be surrounded in all three directions in space by the coil pairs, which would impede access to the examination zone. The coils 5a, 6a are therefore arranged above and the coils 5b, 6b beneath the patient 1. The coils 5a, 5b generate a magnetic field component of which the direction is oriented perpendicular to the coil axis 8. Furthermore, the coils 6a, 6b generate a magnetic field component of which the direction is oriented perpendicular to the coil axis 8 and perpendicular to the direction of the magnetic field component that is generated by the coil pair 5a, 5b. The coils 5a, 5b, 6a, 6b thus generate magnetic field components that are oriented perpendicular to their coil axis. Such coils are not of the Helmholtz type and are known from magnetic resonance apparatuses having open magnets (open MRI), in which a high-frequency coil pair that is able to generate a horizontal, time-variable magnetic field is arranged above and beneath the patient. The construction of these known coils 5a, 5b, 6a, 6b is not explained in detail here.

The coil pairs 4a, 4b ... 6a, 6b thus generate the time-variable, second magnetic field, by means of which the first sub-zone 301 of the first magnetic field in the examination zone, which is here three-dimensional but may alternatively be two-dimensional, can be moved.

The movement of the first sub-zone 301 in the examination zone leads to a change in the magnetization of the magnetic particles 102, with the result that signals are induced in a suitable receiving coil.

FIG. 1 shows schematically a receiving coil 7, which is adapted in such a way that signals can be induced in the receiving coil 7 on the basis of a changing magnetization in the examination zone. In principle, any of the field-generating coil pairs 3a, 3b ... 6a, 6b could be used for that purpose. However, one or even several separate receiving coils 7 have the advantage that they can be arranged and switched independently of the field-generating coils 3a, 3b ... 6a, 6b and produce an improved signal-to-noise ratio.

If the magnetization change is to be determined in all three directions in space, then at least one receiving coil that is able to receive the corresponding directional component of the magnetization change is required for each direction in space.

The induction of signals in a receiving coil on the basis of the changing magnetization of the magnetic particles is described in more detail in DE 101 51 778, to which the reader is referred.

Figure 4:
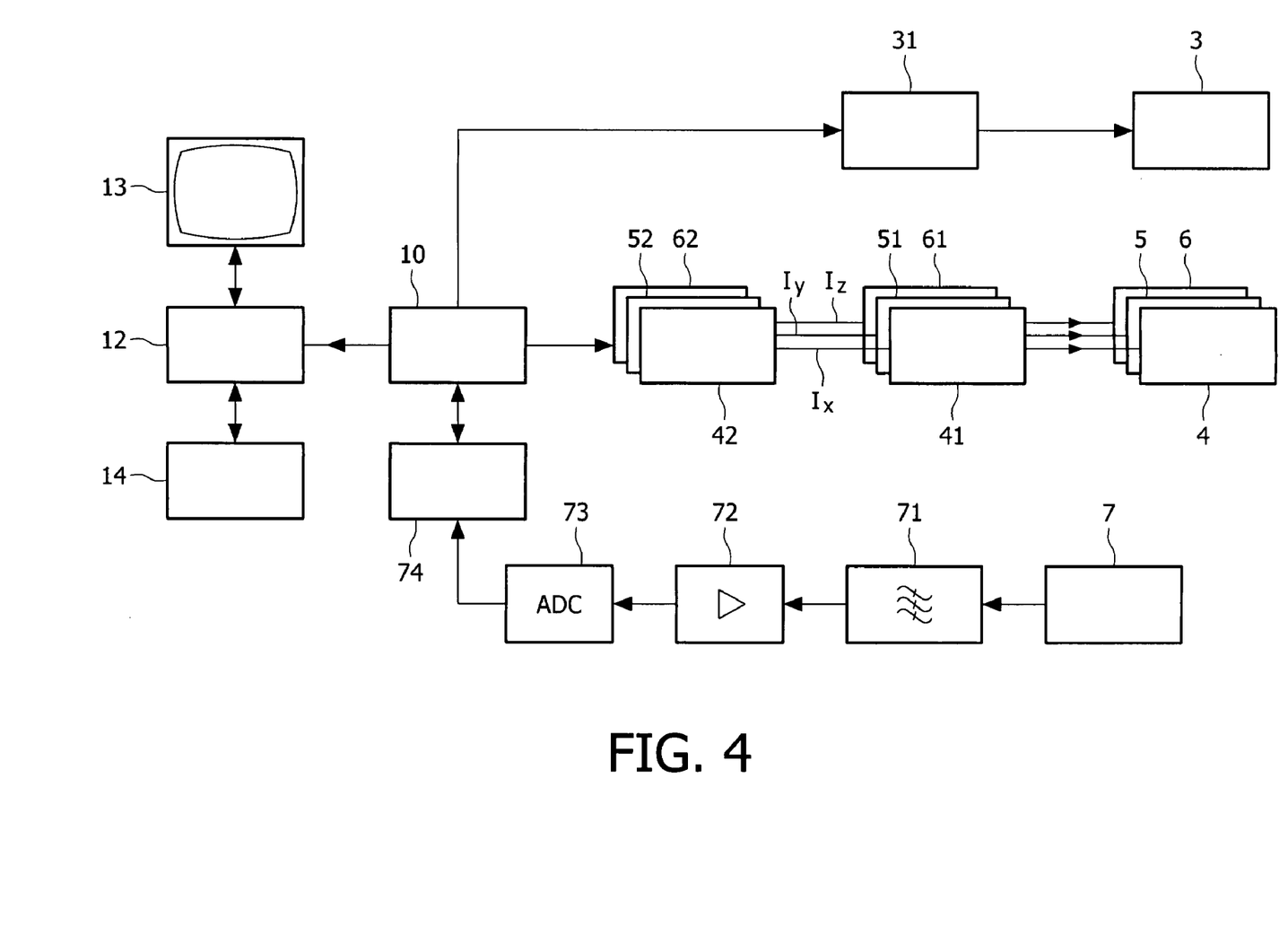
FIG. 4 shows a block diagram of the apparatus of FIG. 1.

FIG. 4 shows a block diagram of the apparatus 9 shown in FIG. 1. The coil pair 3a, 3b is shown schematically in FIG. 4 and for the sake of clarity is denoted by the reference numeral 3. The same applies to the coil pairs 4a, 4b ... 6a, 6b.

The coil pair 3 is supplied with a direct current from a controllable current source 31, which is controlled by the control unit 10. The control unit 10 is connected to a computer 12 with a monitor 13 for displaying the distribution of magnetic particles in the examination zone and with an input unit 14, for example, a keyboard 14.

The coil pairs 4, 5, 6 are connected to current amplifiers 41, 51, 61, from which they receive their currents. The current amplifiers 41, 51, 61 are in turn connected to a respective alternating current source 42, 52, 62, which determine the time characteristic of the currents $I_x$, $I_y$, $I_z$, to be amplified. The alternating current sources 42, 52, 62 are controlled by the control unit 10.

Furthermore, the receiving coil (acquisition means) 7 is illustrated schematically in FIG. 4. The signals induced in the receiving coil 7 are supplied to a filter unit 71, which filters signals oscillating at the fundamental frequency or the fundamental frequencies. The filtered signals are then transferred via an amplifier unit 72 to an analog-to-digital converter 73 (ADC). The digitized signals produced by the analog-to-digital converter 73 are supplied to an image-processing unit (evaluating unit) 74, which reconstructs the spatial distribution of the magnetic particles from these signals and from the particular position that is assumed by the first sub-zone 301 of the first magnetic field in the examination zone during reception of the respective signal and is received by the image processing unit 74 from the control unit 10. The reconstructed spatial distribution of the magnetic particles is finally transferred via the control unit 10 to the computer 12, which displays it on the monitor 13.

Figure 5:
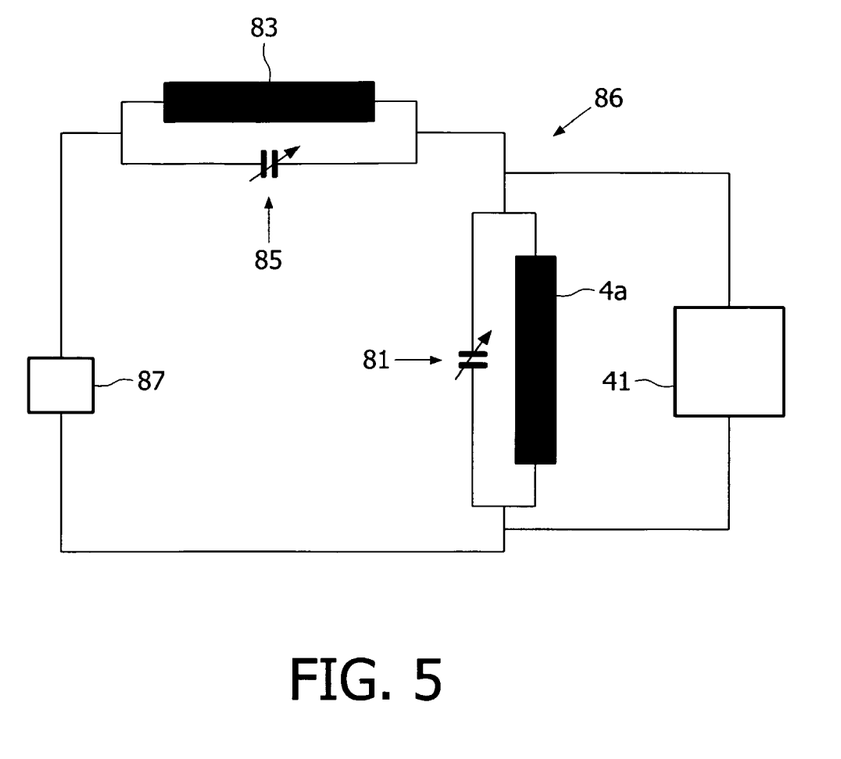
FIG. 5 shows a circuit diagram of a single-resonance coil system.
Figure 6:
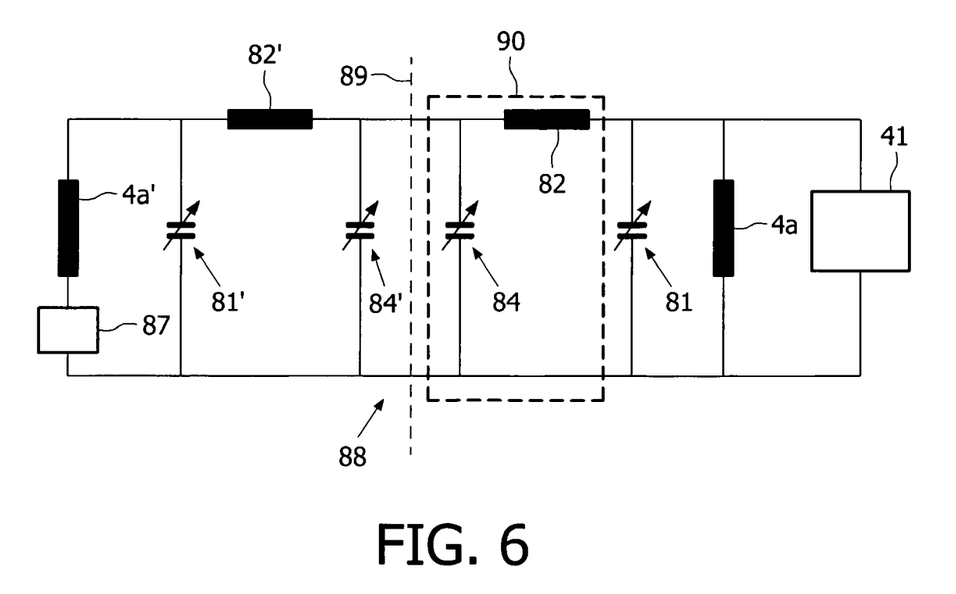
FIG. 6 shows a circuit diagram of a multiresonance coil system.

FIGS. 5 and 6 show preferred circuit diagrams of two magnetic means, which contain the field-generating coil 4a and the current amplifier 41. The field-generating coils 4b ... 6b and the associated current amplifiers 41, 51, 61 are preferably correspondingly configured.

FIG. 5 shows a single-resonance coil system 86, which comprises the field-generating coil 4a that is connected in parallel with an adjustable capacitor 81. The field-generating coil 4a is thereby rendered resonant for one fundamental frequency, wherein the resonant fundamental frequency can be set by adjusting a desired capacitance at the capacitor 81 and by selecting a coil 4a with desired inductance. This resonant circuit comprising the field-generating coil 4a and the capacitor 81 is connected in parallel with the current amplifier 41, which delivers a time-variable current. Using such a resonant circuit, a second magnetic field can be generated having a higher amplitude than if the current amplifier 41 is connected directly to the field-generating coil 4a, that is, without the additional parallel capacitor 81. If, therefore, a specific amplitude of the second magnetic field is needed, then with the use of the illustrated resonant circuit it is possible to use a current amplifier that has a lower amplification factor and is therefore less expensive than a current amplifier that is needed when no such resonant circuit is used.

To generate the slowly variable offsets of the second magnetic field, a low-frequency current source 87 can be used, which is connected parallel to the resonant circuit comprising the capacitor 81 and the field-generating coil 4a. Such a low-frequency current source 87 has a low impedance for the high fundamental frequencies, however, so that the resonant circuit would be short-circuited by the current source 87. The circuit must therefore have additional components that have a high impedance for the high fundamental frequencies, but at the same time allow low frequencies through, that is, the frequencies at which the offsets oscillate. A simple technical solution is a rejector circuit, comprising a further coil 83 and parallel thereto a capacitor 85, which is arranged between the current source 87 and the resonant circuit comprising the capacitor 81 and the field-generating coil 4a.

The exact dimensions of the coils and capacitors and the practical construction of the coils (e.g. annular coil with large geometrical dimensions), which are required in order to render the field-generating coil 4a resonant for a fundamental frequency and at the same time to allow slowly variable offsets of the second magnetic field, are known to the person skilled in the art, so that further detail is unnecessary here.

Preferably, the inductances of the coils in FIG. 5 are substantially identical, that is, they differ at most by one order of magnitude. In order to excite the field-generating coil 4a technically, as is generally known the current amplifier 41 can be provided with a suitable matching circuit, which comprises, for example, a transformer with a series-connected capacitor, or a suitable capacitive voltage divider, the total capacitance of which is preferably identical with the capacitance of the capacitor 81 and/or with the capacitance of the capacitor 85. Alternatively, coupling to the field-generating coil 4a can be effected inductively.

Since the circuit according to FIG. 5 has just one resonant fundamental frequency, this circuit is known as a single-resonance coil system 86. In order to change the resonant fundamental frequency, the capacitance of the capacitors 81, 85 can be changed. In order to change the resonant fundamental frequency during a measurement, so as to pass through a frequency range, the capacitors are automatically variable, for example, by add-on smaller capacitors or because the capacitors 81, 85 are motor-adjustable variable capacitors. Alternatively, other known methods can be used to change the resonant fundamental frequency of the single-resonance coil system 86; for example, adjustable auxiliary coils can be used or magnetic materials can be brought towards the coils shown in FIG. 5.

If a second magnetic field is desired, which is generated by the field-generating coil 4a and has two fundamental frequencies, then a multiresonance coil system 88 as shown in FIG. 6 can be used. To the right of the mirror line 89 in FIG. 6, the multiresonance coil system 88 comprises the field-generating coil 4a, with which the capacitor 81 is connected in parallel. The coil 4a is additionally connected to the current amplifier 41. The multiresonance coil system moreover comprises to the right of the mirror line 89 in FIG. 6 a further coil 82 and a further adjustable capacitor 84. The effect of this circuit arranged to the right of the mirror line 89 in FIG. 6 is that the field-generating coil 4a has two resonant fundamental frequencies, that is, this field-generating coil 4a can be used to generate a second magnetic field that oscillates with two resonant fundamental frequencies. If, for example, the further coil 82 has a larger inductance than the field-generating coil 4a and if the capacitances of the capacitors 81 and 84 are identical, then the resonant fundamental frequency that is generated by the additional components 82, 84 is lower than the fundamental frequency that is generated with a circuit without the additional components 82, 84, as illustrated in FIG. 5.

If a low-frequency current source is connected to the circuit illustrated to the right of the mirror line 89 in FIG. 6, in order to generate the slowly variable offsets of the second magnetic field, then as described above in connection with FIG. 5 the circuit would be short-circuited, since the current source for the high fundamental frequencies has a low impedance. The capacitors and coils are therefore reflected at the mirror line, so that the capacitors 81' and 84' and the coils 4a' and 82' are arranged mirror-symmetrically with respect to the mirror line 89 to the capacitors 81, 84 and the coils 4a and 82. The low-frequency current source 87 is connected in series with the coil 4a'.

If more than two resonant fundamental frequencies are to be generated, then for each further desired resonant fundamental frequency the portion of the circuit that is outlined in FIG. 6 by a dotted line 90 can be arranged an additional number of times between the mirror line 89 and the resonant circuit comprising the capacitor 81 and the field-generating coil 4a. The added coils and capacitors would then have to be reflected in turn at the mirror line 89, of course.

The invention is not limited to the represented single-resonance and multiresonance coil systems. On the contrary, in accordance with the invention use can be made of any circuit arrangement of coils and capacitors that enables a second magnetic field to be generated that has both one or more high fundamental frequencies as well as low frequencies that lie close to zero frequency. In known manner, also other resonant structural elements can be used, such as, for example, electromechanical resonators (piezos) or resonators that are based on transit-time effects.

The time-variable second magnetic field $H_2(t)$ can be parameterized as follows:

$$H_2(t) = \begin{pmatrix} a_x(t)\sin(\omega_x(t)t + \varphi_x(t)) + v_x(t) \\ a_y(t)\sin(\omega_y(t)t + \varphi y(t)) + v_y(t) \\ a_z(t)\sin(\omega_z(t)t + \varphi_z(t)) + v_z(t) \end{pmatrix} \quad (1)$$

Here, $\alpha_{x,y,z}(t)$ are amplitudes, $\omega_{x,y,z}(t)$ are fundamental frequencies, $\phi_{x,y,z}(t)$ are phase shifts and $v_{x,y,z}(t)$ are offsets. The amplitudes, fundamental frequencies, phase shifts and offsets vary more slowly with time t than $\sin(\omega_x t)$, $\sin(\omega_y t)$ and $\sin(\omega_z t)$, that is, the respective Fourier transform of $\alpha_{x,y,z}(t)$, $\omega_{x,y,z}(t)$, $\phi_{x,y,z}(t)$ and $v_{x,y,z}(t)$ has exclusively values at frequencies that are smaller than any of the fundamental frequencies $\omega_{x,y,z}$.

Alternatively, the time-variable second magnetic field can be parameterized by the following equation:

$$H_2(t) = \sum_i H_2^{(i)}(t) + \begin{pmatrix} v_x(t) \\ v_y(t) \\ v_z(t) \end{pmatrix} \text{ with} \quad (2)$$

$$H_2^{(i)}(t) = \begin{pmatrix} a_x^{(i)}(t)\sin(\omega_x^{(i)}(t)t + \varphi_x^{(i)}(t)) \\ a_y^{(i)}(t)\sin(\omega_y^{(i)}(t)t + \varphi_y^{(i)}(t)) \\ a_z^{(i)}(t)\sin(\omega_z^{(i)}(t)t + \varphi_z^{(i)}(t)) \end{pmatrix}.$$

That is, the second magnetic field $H_2(t)$ can alternatively comprise a sum of partial magnetic fields $$\sum_i H_2^{(i)}(t),$$

wherein here too for each partial magnetic field $H_2^{(i)}(t)$ the amplitudes $\alpha_{x,y,z}^{(i)}(t)$, fundamental frequencies $\omega_{x,y,z}^{(i)}(t)$ and phase shifts $\phi_{x,y,z}^{(i)}(t)$ vary more slowly with time t than $\sin(\omega_x^{(i)} t)$, $\sin(\omega_y^{(i)} t)$ and $\sin(\omega_z^{(i)} t)$, that is, the respective Fourier transform of $\alpha_{x,y,z}^{(i)}(t)$, $\omega_{x,y,z}^{(i)}(t)$ $\phi_{x,y,z}^{(i)}(t)$ and $v_{x,y,z}^{(i)}(t)$ has exclusively values at frequencies that are smaller than any of the fundamental frequencies $\omega_{x,y,z}^{(i)}$.

Within the scope of the present invention, only the time dependency of the second magnetic field $H_2(t)$ is considered. It is clear, however, that because of the finite dimensions of the field-generating coils, it is impossible for there to be a completely spatially homogeneous second magnetic field present, so that the second magnetic field is also dependent on location $H_2(x, y, z, t)$. The separate consideration of the time dependency is possible here, given that the wavelength is large compared with the dimensions of the coils 4, 5, 6, that is, $H_2(x, y, z, t) = F(x, x, z) \cdot H_2(t)$, in which $F(x, y, z)$ is a function that describes the location-dependency of the second magnetic field. In this context, the wavelength is the wavelength of the electromagnetic wave of the second magnetic field. This wavelength is in the kilometer range in the case of the fundamental frequencies used here, so that it is large in comparison with the coils, the dimensions of which lie at most within the meter range.

In this exemplary embodiment the second magnetic field $H_2(t)$ has three spatial components $H_{2,x}(t)$, $H_{2,y}(t)$ and $H_{2,z}(t)$ orthogonal to one another, so that the first sub-zone 301 can be moved in three-dimensional space. In different constructions, the second magnetic field $H_2(t)$ could also have just two spatial components orthogonal to one another, so that the first sub-zone 301 could be moved in one plane.

The spatial components of the second magnetic field generated by field-generating coils need not be oriented orthogonal to one another. The field-generating coils can also generate spatial components of the second magnetic field that are directed in different directions in space not orthogonal to one another. A second magnetic field with spatial components oriented in this manner is easily transformable to a second magnetic field as per the equation (1) or (2), so that the explanations for the second magnetic field with orthogonally oriented spatial components are applicable correspondingly.

The time variation of the offsets $v_{x,y,z}(t)$ leads to frequency components of the second magnetic field $H_2(t)$ that lie in a first frequency range $\Delta\omega_v$, that is, when the second magnetic field $H_2(t)$ is subject to Fourier transform the time variation of the offsets $v_{x,y,z}(t)$ leads to values of the Fourier transforms in the first frequency range $\Delta w_v$. The first frequency range $\Delta\omega_v$ comprises exclusively values that are smaller than any of the fundamental frequencies. In particular, the first frequency range $\Delta\omega_v$ comprises preferably values that lie close to zero frequency and amount to only a few Hertz, that is, for example, 0.1 to 100 Hz. The width of the first frequency range is preferably less than ten times and especially less than one hundred times the smallest fundamental frequency. Furthermore, preferably every fundamental frequency is greater than ten times and especially greater than one hundred times the largest frequency in the first frequency range $\Delta\omega_v$.

High fundamental frequencies lead to a more rapid movement of the first sub-zone of the first magnetic field and hence to higher signals in the receiving coil 7, but also increase the known patient noise, which increases as the fundamental frequency increases. Preferred fundamental frequencies at which the signal-to-noise ratio of the signals acquired with the receiving coil 7 is sufficient in order to reconstruct images of very good quality, as described below, lie in a range from 20 kHz to 1 MHz. If SQUID detectors known from magnetic resonance spectroscopy are used as acquisition means, then the fundamental frequencies can be selected to be smaller by a factor of 1000.

The slow variation in the offsets, in addition to the rapid movement of the first sub-zone 301 caused by the portions of the second magnetic field oscillating at the fundamental frequencies, causes an additional slow shift of the first sub-zone 301, with the result that a larger region can be covered by the first sub-zone 301 and the examination zone is enlarged. The offsets change so slowly that they make no or hardly any contribution to the reconstruction explained below of an image of the examination zone, since the signals induced by the change in the offsets are very small owing to the slow movement of the first sub-zone and have no or hardly any influence on the signals acquired by the receiving coil 7.

The time variation of the offsets, that is, the shift of the first sub-zone 301 caused thereby, should be selected so that the first sub-zone 301 of the first magnetic field covers the entire examination zone, which has been defined by a radiologist for example.

As is known, for example, from magnetic resonance spectroscopy, the application of time-variable magnetic fields to biological tissue leads to warming and, if warming is immoderate, to damage of the tissue. Warming depends substantially on the product of amplitude and fundamental frequency, the form of the magnetic field and the type of tissue exposed to the magnetic field. The amplitudes and fundamental frequencies of the second magnetic field are to be selected so that no tissue is damaged. For example, if a large region, such as, for example, the gastrointestinal tract of a human patient, is to be exposed to the second magnetic field, the amplitude should be less than 20 mT and the fundamental frequency should be less than 100 kHz.

The slow time variation of the amplitudes, phase shifts and fundamental frequencies, as is known from known amplitude, phase and frequency modulation techniques, leads to frequency components of the second magnetic field that are arranged around the fundamental frequencies. Preferably the apparatus 9 according to the invention is constructed so that the result of the time variation of the amplitudes, phase shifts and fundamental frequencies is that the Fourier transform of the second magnetic field comprises values in frequency ranges $\Delta\omega_{x,y,z}$ and $\Delta\omega_{x,y,z}^{(i)}$ arranged around the fundamental frequencies, which ranges have a relative breadth of $\Delta\omega_{x,y,z}^{(i)}/\omega_{x,y,z}^{(i)}<0.1$ respectively $\Delta\omega_{x,y,z}/\omega_{x,y,z}<0.1$ and more preferably of $\Delta\omega_{x,y,z}^{(i)}/\omega_{x,y,z}^{(i)}<0.01$ respectively $\Delta\omega_{x,y,z}/\omega_{x,y,z}<0.01$. In absolute terms, the breadth of the frequency ranges that are arranged around the fundamental frequencies is preferably of the same order of magnitude as the breadth of the first frequency range $\Delta\omega_v$. In particular, the breadths of the frequency ranges arranged around the fundamental frequencies and of the first frequency range are preferably the same.

In another preferred embodiment, the amplitudes, phase shifts and fundamental frequencies are preferably independent of time.

Outside the frequency ranges that are arranged around the fundamental frequencies, and outside the frequency range $\Delta\omega_v$, the Fourier transform of the second magnetic field preferably has no values. The effect of this is that the signals induced by the rapid changes in the second magnetic field are not disrupted by frequency components that do not lie within the frequency ranges, whereby the image quality is improved.

FIGS. 7 to 10 are representations of the second magnetic field, wherein in each case a spatial component of the second magnetic field is plotted over a spatial component of the second magnetic field orthogonal thereto.

Figure 7:
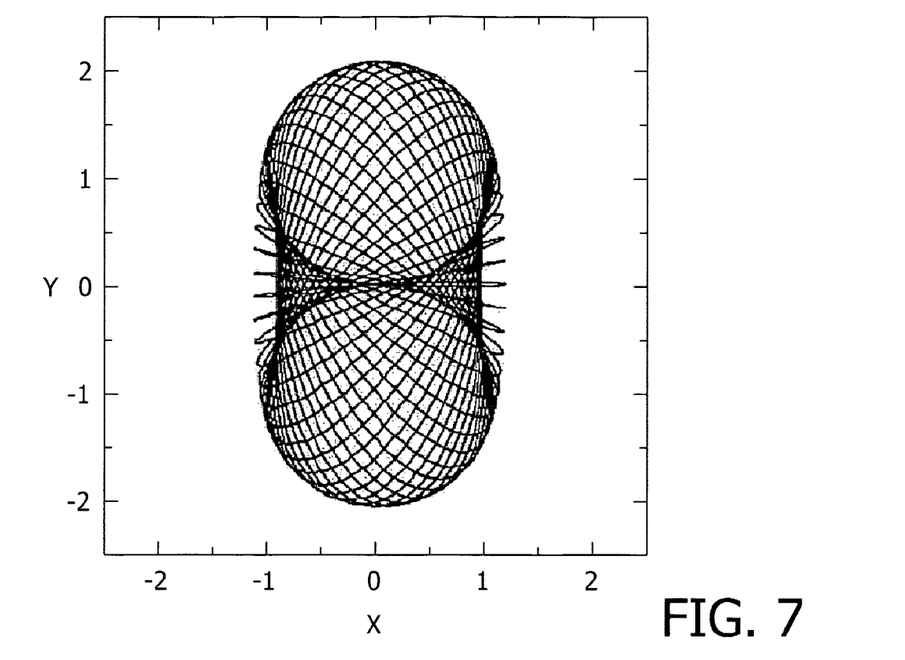
FIGS. 7 to 10 show two-dimensional representations of two spatial components orthogonal to one another of the time-variable second magnetic field.

In FIG. 7, a spatial component $H_{2,y}(t)=\cos(29t)+0.1\cos(30t)$ of one embodiment of the second magnetic field $H_2(t)$ is plotted against a second spatial component $H_{2,x}(t)=\sin(29t)-\sin(30t)$ orthogonal thereto of this second magnetic field. The numerical values at the vertical and at the horizontal axis in FIG. 7 are specified in arbitrary units. The same applies to the numerical values in FIGS. 8 to 10.

Figure 8:
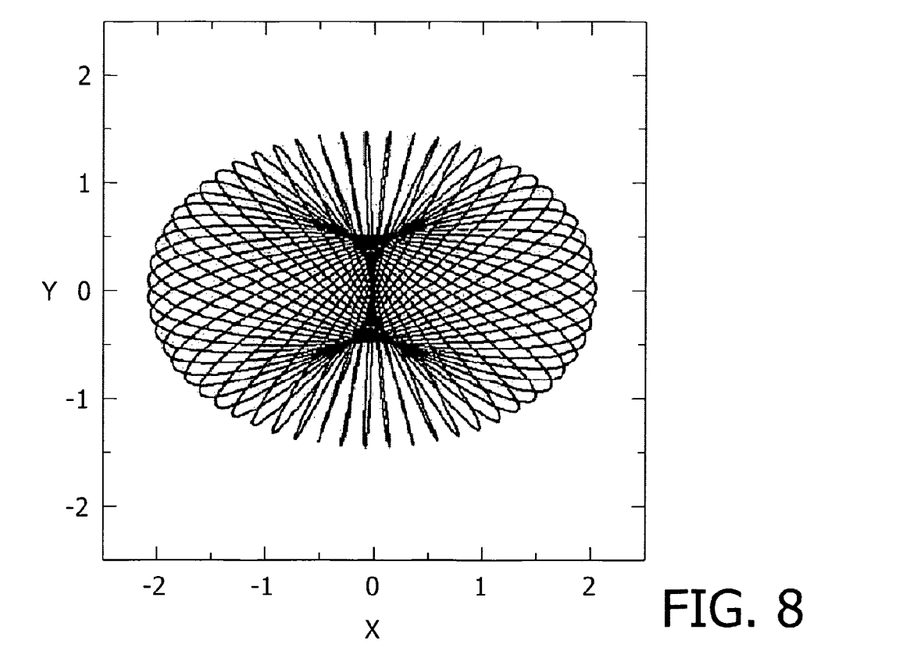

In FIG. 8, a spatial component $H_{2,y}(t)=\cos(29t)+\cos(30t)$ of a different embodiment of the second magnetic field $H_2(t)$ is plotted against a spatial component $H_{2,x}(t)=\sin(29t)-0.5\sin(30t)$ orthogonal thereto of this embodiment of the second magnetic field.

Figure 9:
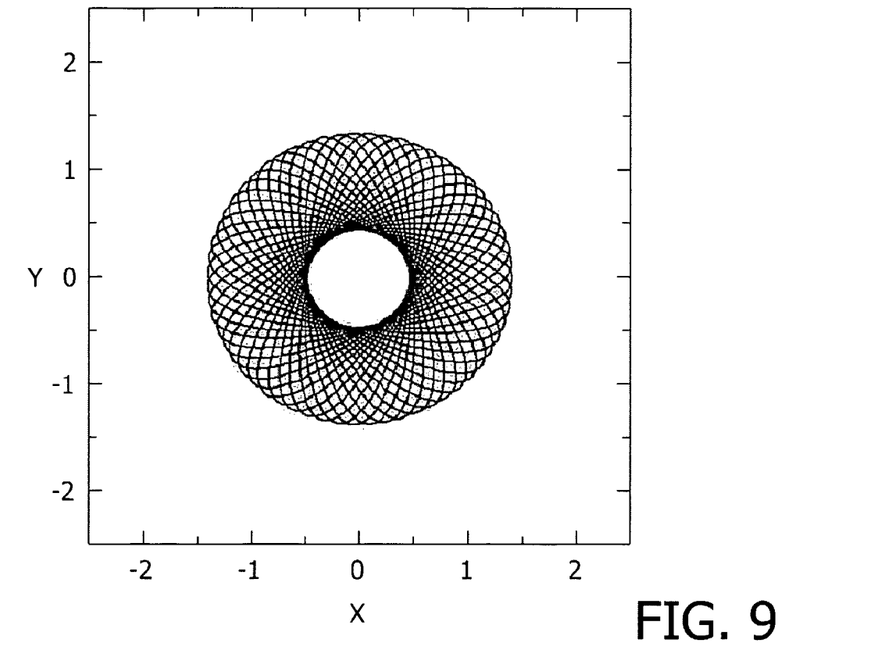

In FIG. 9, a spatial component $H_{2,y}(t)=\cos(29t)+0.5\cos(30t)$ of a further embodiment of the second magnetic field $H_2(t)$ is plotted against a spatial component $H_{2,x}(t)=\sin(29t)-0.5\sin(30t)$ perpendicular thereto of this embodiment of the second magnetic field.

Figure 10:
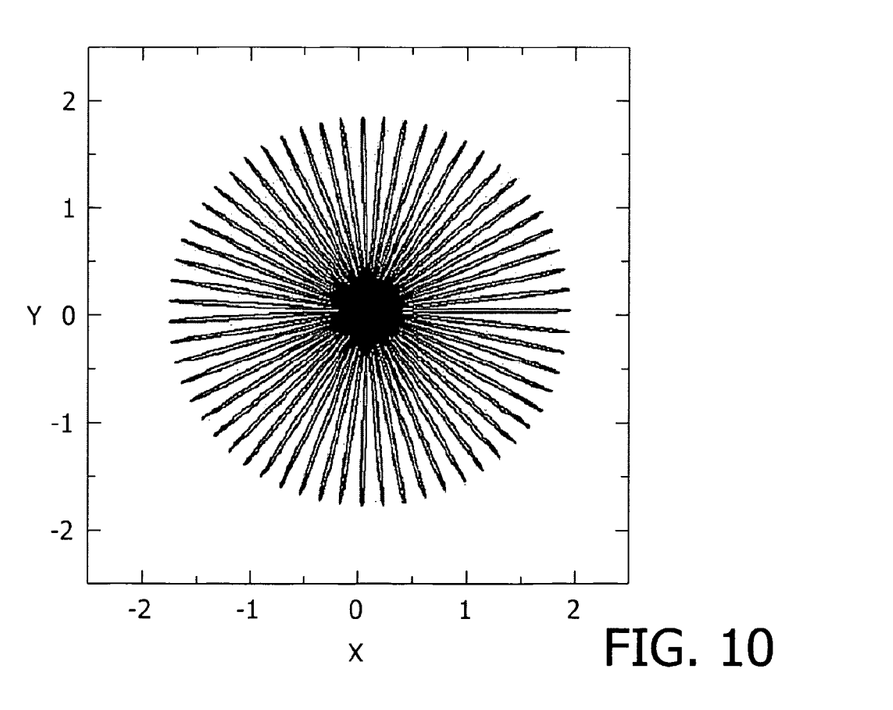

In FIG. 10, a spatial component $H_{2,y}(t)=\cos(29t)+\cos(30t)$ of a further embodiment of the second magnetic field $H_2(t)$ is plotted against a spatial component $H_{2,x}(t)=\sin(29t)-\sin(30t)$ perpendicular thereto of this embodiment of the second magnetic field.

The use of a second magnetic field according to the embodiments shown in FIGS. 7 to 10 leads to good quality images of the spatial distribution of magnetic particles in the examination zone.

The spatial components of the second magnetic field specified in FIGS. 7 to 10 and in the associated description can easily be rendered in a form according to equation (1) by trigonometric conversions, as described in the following. These spatial components can be represented generally by $$H_{2,x}(t)=\cos(29t)+a\cos(30t) \quad (3)$$

$$H_{2,y}(t)=\sin(29t)+b\sin(30t) \quad (4)$$

These spatial components can be converted so that they have the following construction:

$$H_{2,x}(t) = \sqrt{1 + a^2 + 2a\cos(t)} \sin(29t + \varphi_x(t)), \quad (5)$$
$$\tan(\varphi_x(t)) = -\frac{1 + a\cos(t)}{a\sin(t)} \text{ and}$$

$$H_{2,y}(t) = \sqrt{1 + b^2 + 2b\cos(t)} \sin(29t + \varphi_y(t)), \quad (6)$$
$$\tan(\varphi_y(t)) = -\frac{1 + b\sin(t)}{b\cos(t)}.$$

The variables a and b are arbitrary real numbers, so that the equations (5) and (6) correspond to a form of the second magnetic field according to equation (1).

A time-variable second magnetic field according to FIGS. 7 to 10 causes a movement of the first sub-zone 301 substantially along the path shown in the respective Figures. The qualification "substantially" is used here since the correlation between the time variation of the second magnetic field in a direction in space and the shift of the first sub-zone 301 is not linear, since the second magnetic field does not change linearly with location. The result of this is that the first sub-zone 301 of the first magnetic field does not move exactly on the paths shown.

Alternatively, the second magnetic field can be adjusted so that the path on which the first sub-zone 301 moves through the examination zone describes a Lissajous figure.

The proportions of the second magnetic field of which the Fourier transforms lie in the first frequency range $\Delta\omega_v$, that is, the slowly variable components of the second frequency range that are caused by the time dependency of the offsets $v_{x,y,z}(t)$, lead to an overall shift in the paths shown in FIGS. 7 to 10, the result of which is that the first sub-zone 301 spreads over a relatively large region in the patient 1, whereby the examination zone is enlarged.

The second magnetic field is designed in such a way that the time derivative of the second magnetic field is substantially identical in each direction in space, that is to say, values that are produced by applying a measure of the magnitude of the time derivative for the particular spatial component differ at most by a factor of five. This means two time derivatives for different spatial components are identical, when this measure applied to the time derivative of a spatial component of the second magnetic field yields a value that is not greater than five times and not less than one fifth of the value that is produced when this measure is applied to the time derivative of the other spatial component of the second magnetic field. The first sub-zone is therefore moved in different directions in space at speeds that do not differ significantly, whereby the resolution of an examination zone image, reconstructed as described below, is not significantly different in different directions in space, which improves the image quality.

A measure of the magnitude of the time derivative is, for example, the quadratic mean of the time derivative of a spatial component over time. Alternatively, the measure can be the maximum of the time derivative of a spatial component of the second magnetic field.

A substantially identical speed of the first sub-zone 301 for different spatial components can be achieved, for example, for the reason that the product of fundamental frequency and amplitude for each spatial component of the second magnetic field $H_2(t)$ or for each spatial component of each partial magnetic field $H_2^{(i)}(t)$ is substantially the same.

Preferably, the second magnetic field is designed in such a way that fundamental frequencies for each spatial component of the second magnetic field or for each spatial component of each partial magnetic field $H_2^{(i)}(t)$ are substantially identical. This has the advantage that the signal-to-noise ratio for signals that have been acquired during movement of the first sub-zone in different directions is not significantly different, which leads to an improved image quality.

In other embodiments, the fundamental frequency can vary with time and in particular can increase with time. The remarks made above in connection with the Fourier transform then relate to a piecewise temporal Fourier transformation; that is to say, a Fourier transform is formed over a predetermined period which is preferably of the same order of magnitude as the reciprocal value of the breadth of the frequency ranges that are arranged around the fundamental frequencies owing to the time dependency of amplitudes, phase shifts and fundamental frequencies.

A minimum distance can be entered in the apparatus 9 via the input device 14, the control unit 10 controlling the alternating current sources 42, 52, 62 in such a way and hence constructing the second magnetic field in such a way that the position of the first sub-zone changes so that for each point in the examination zone the distance between the middle of the first sub-zone and the respective point is at least at one instant less than the entered minimum distance. In this manner it is possible to ensure that each portion of the examination zone is covered by the first sub-zone 301. It should be borne in mind here that, as already remarked above and stated in DE 101 51 778, there is a non-linear correlation between the shift of the first sub-zone 301 and the change in the second magnetic field in a specific direction in space. The correlation between the change in the second magnetic field and the shift of the first sub-zone can be determined, for example, empirically, and can be saved in table form in the memory 10. If a minimum distance is specified, then having regard to the tables the control unit can determine a path of the first sub-zone 301 in the examination zone and the associated time-variable second magnetic field so that the minimum distance is taken into account.

In order not to reduce the resolution of the apparatus 9 by specifying a minimum distance that is unduly large, the minimum distance is specified to be less than ten times the resolution limit of the apparatus 9. Alternatively, the minimum distance is specified to be less than three times the resolution limit.

The resolution limit is defined by means of two areas in the examination zone that contain magnetic particles and are as small as possible but large enough to generate signals that can be acquired by the receiving coil. The resolution limit is the distance between these two areas at which these areas can still just be differentiated in a reconstructed image of the examination zone, that is to say, with a smaller distance it would no longer be possible to distinguish between these two areas in the reconstructed image. The smaller the resolution limit is, the greater therefore the resolution.

The spatial resolution of the apparatus 9 is determined by the size of the first sub-zone 301. This size depends firstly on the gradient strength of the gradient field that is generated by the coil pair 3a, 3b, and also on the magnitude of the magnetic field required for a saturation of the magnetization of the magnetic particles. The magnitude of this magnetic field amounts to 1 mT at a diameter of the sphere illustrated in FIG. 3 of 10 µm and to 100 µT at a diameter of 100 µm. In the case of the last-mentioned value and at a gradient of the magnetic field of 0.2 T/m, the first sub-zone 301 has a diameter of about 1 mm.

Figure 11:
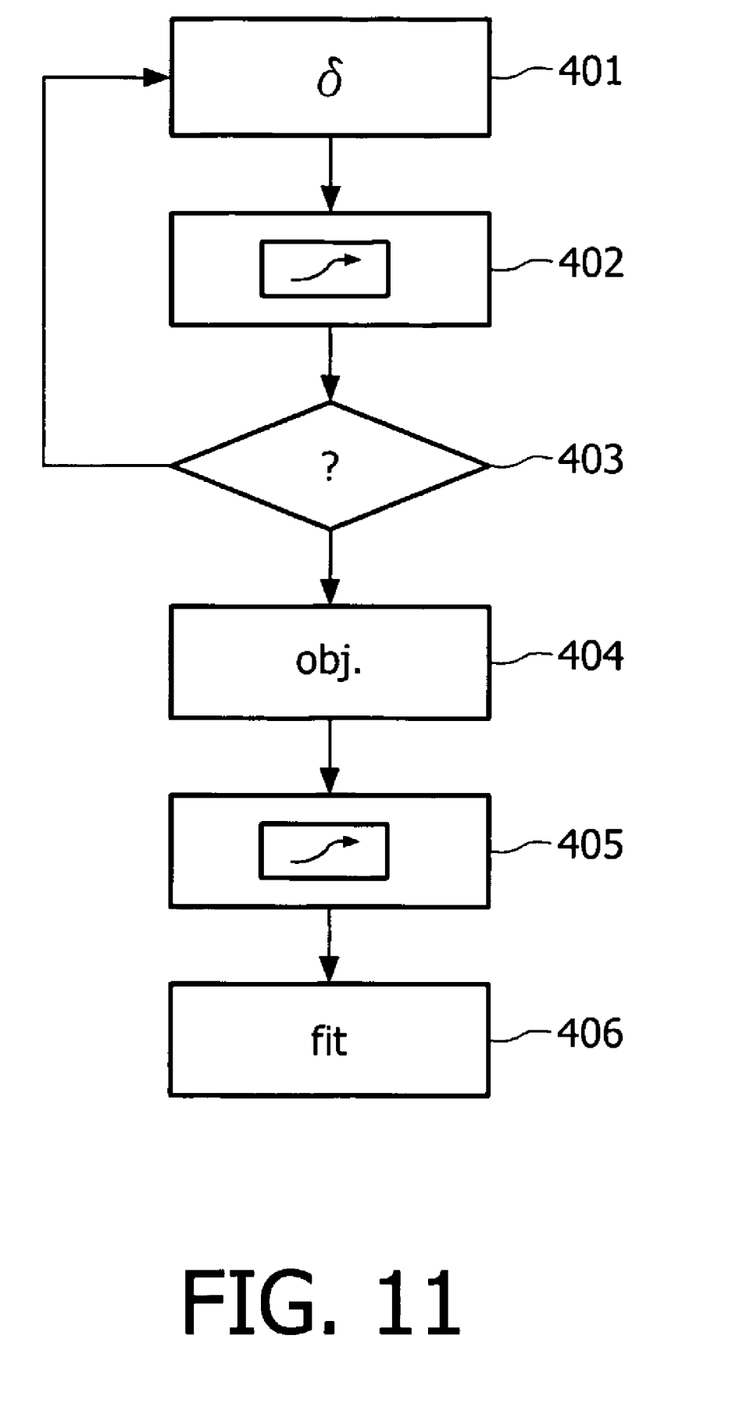
FIG. 11 shows a flow chart of a method in accordance with the invention.

Using the flow chart from FIG. 11, there follows a description of how an examination zone image containing information concerning the distribution of the magnetic particles in the examination zone can be reconstructed from the signals acquired at the receiving coil 7.

First of all, in step 401 a delta probe, that is to say, a probe of finite yet very small dimensions, for example, 1 mm³, is placed at one of a predetermined quantity of points in the examination zone. This quantity of points can comprise, for example, points that are arranged in Cartesian format in the examination zone, adjacent points having a spacing that is identical with the resolution limit.

Then, in step 402, the first and the second magnetic fields are switched on, so that the first sub-zone 301 moves within the examination zone owing to the effect of the second magnetic field. At the same time, the receiving coil 7 acquires signals that are induced in the receiving coil 7 owing to the changing magnetization in the examination zone.

In step 403, it is ascertained whether the delta probe has been placed at all predetermined points in the examination zone. If this is the case, then the process continues with step 204. Otherwise, in step 401 the delta probe is placed at a point at which it has not yet been placed, and induced signals are acquired in step 402 for this new location of the delta probe.

In step 404, an object containing magnetic particles is placed in the examination zone, the distribution of which magnetic particles in the object is to be determined. The object can be, for example, a patient, who has ingested a liquid or a meal containing magnetic particles, which are located in his gastrointestinal tract at the time of measuring.

In step 405, the first and second magnetic fields are switched on, so that the first sub-zone 301 moves within the examination zone owing to the effect of the second magnetic field. At the same time, induced signals are acquired in the receiving coil 7.

In step 406, an image of the examination zone is reconstructed from the signals acquired in steps 402 and 405. For that purpose the following assumption is made:

$$S_o(r(t)) = \sum_p \alpha_p S_p(r(t)). \quad (3)$$

It is thus assumed that with no disruptive external influences a signal $S_o(r(t))$ that has been acquired by the receiving coil while the object was located in the examination zone and the first sub-zone was located at the point r(t) in the examination zone equals the sum $$\sum_p \alpha_p S_p(r(t)).$$

In this connection, $\alpha_p$ is a factor that is a measure of the concentration of the magnetic particles at the particular point in the examination zone, here denoted by p. Furthermore, $S_p(r(t))$ is the signal acquired while the delta probe was located at the point p and the first sub-zone 301 was located at the point r(t) in the examination zone.

The factors $\alpha_p$ are adapted by means of the known least square fitting method, that is to say, the factors $\alpha_p$ are determined so that the expression $$\int_T \left[ S_o(r(t)) - \sum_p \alpha_p S_p(r(t)) \right]^2 dt \quad (4)$$

is minimized. The integration over time t is in this case carried out across the entire period T during which signals that are used for the reconstruction were acquired.

The resulting factors $\alpha_p$ are a measure of the concentration of magnetic particles at the particular point denoted by p in the examination zone and are thus the image of the examination zone that yields information concerning the distribution of the magnetic particles in the examination zone.

The method according to the invention is not limited to the reconstruction described. On the contrary, the invention includes any reconstruction method that can extract information concerning the distribution of the magnetic particles in the examination zone from the acquired signals. For example, the reconstruction methods disclosed in DE 101 51 778 can be used.

The invention claimed is:

1. A method of determining a spatial distribution of magnetic particles (102) in an examination zone with a first, time-constant magnetic field and a second, time-variable magnetic field, wherein the second, time-variable magnetic field has a fundamental frequency and an amplitude in each spatial component and the time derivative of the second magnetic field is substantially identical for each spatial component, or the second, time-variable magnetic field encompasses a sum of several second, time-variable partial magnetic fields, each partial magnetic field having a fundamental frequency and an amplitude in each spatial component and the time derivative of the second magnetic field and/or of the second partial magnetic fields being substantially identical for each spatial component.

2. A method as claimed in claim 1, characterized in that the second magnetic field ($H_2$) and/or each second partial magnetic field ($H_2^{(i)}$) are generated so that for the second magnetic field ($H_2$) and/or for each second partial magnetic field ($H_2^{(i)}$) the product of the fundamental frequency ($\omega_{x,y,z}$, $\omega_{x,y,z}^{(i)}$)) and the amplitude ($\alpha_{x,y,z}$, $\alpha_{x,y,z}^{(i)}$) for a spatial component is substantially identical to the product of the fundamental frequency ($\omega_{x,y,z}$, $\omega_{x,y,z}^{(i)}$) and the amplitude ($\alpha_{x,y,z}$, $\alpha_{x,y,z}^{(i)}$) for any other spatial component.

3. A method as claimed in claim 1, characterized in that the second magnetic field ($H_2$) and/or each second partial magnetic field ($H_2^{(i)}$) are generated so that for the second magnetic field ($H^2$) and/or for each second partial magnetic field ($H_2^{(i)}$) the fundamental frequency ($\omega_{x,y,z}$, $\omega_{x,y,z}^{(i)}$) for a spatial component is substantially identical with the fundamental frequency ($\omega_{x,y,z}$, $\omega_{x,y,z}^{(i)}$) for any other spatial component.

4. A method as claimed in claim 1, characterized in that the second magnetic field ($H_2$) is generated so that at least one or each spatial component of the second magnetic field ($H_2$) has a time-variable offset ($v_{x,y,z}$), wherein a temporal Fourier transform of the second magnetic field ($H_2$) has values in a first frequency range ($\Delta\omega_v$), which are caused by the offsets ($v_{x,y,z}$) the first frequency range ($\Delta\omega_v$) containing values that are smaller than any of the fundamental frequencies ($\omega_{x,y,z}$, $\omega_{x,y,z}^{(i)}$).

5. A method as claimed in claim 4, characterized in that each of the fundamental frequencies ($\omega_{x,y,z}$, $\omega_{x,y,z}^{(i)}$) is larger than ten times and especially larger than one hundred times the largest frequency lying in the first frequency range ($\Delta\omega_v$).

6. A method as claimed in claim 4, characterized in that at least one of the fundamental frequencies ($\omega_{x,y,z}$, $\omega_{x,y,z}^{(i)}$) changes with time and in particular increases with time and in that the temporal Fourier transform is a piecewise temporal Fourier transform, which is determined for a predetermined time interval.

7. A method as claimed in claim 1, characterized in that the second magnetic field ($H_2$) is generated so that the position of the first sub-zone (301) changes in such a way that for each point in the examination zone the distance between the center of the first sub-zone (301) and the respective point is at least at one instant smaller than a predetermined minimum distance.

8. A method as claimed in claim 7, characterized in that the minimum distance is less than ten times a resolution limit and especially less than three times the resolution limit.

9. A method as claimed in claim 1, characterized in that by changing the position in space of the two sub-zones (301, 302) in the examination zone, signals are induced in at least one acquisition means (7), especially in at least one receiving coil, which signals are evaluated to extract information concerning the spatial distribution of the magnetic particles (102) in the examination zone.

10. An apparatus for determining a spatial distribution of magnetic particles (102) in an examination zone with a first, time-constant magnetic field and a second, time-variable magnetic field, wherein the second, time-variable magnetic field ($H_2$) has a fundamental frequency ($\omega_{x,y,z}$) and an amplitude ($\alpha_{x,y,z}$) in each spatial component and the time derivative of the second magnetic field is substantially identical for each spatial component, or the second, time-variable magnetic field ($H_2$) encompasses a sum of several second, time-variable partial magnetic fields ($H_2^{(i)}$), each partial magnetic field ($H_2^{(i)}$) having a fundamental frequency ($\omega_{x,y,z}^{(i)}$) and an amplitude ($\alpha_{x,y,z}^{(i)}$) in each spatial component and the time derivative of the second magnetic field ($H_2$) and/or of the second partial magnetic fields ($H_2^{(i)}$) being substantially identical for each spatial component.

11. An apparatus as claimed in claim 10, characterized in that the second magnetic means comprise a single-resonance or multiresonance coil system (86, 88) having at least one coil (4a) generating the second magnetic field.

12. A computer program for a control unit (10) for controlling first magnetic means (3a, 3b), second magnetic means (4a, 4b, 5a, 5b, 6a, 6b), at least one acquisition means (7) and at least one evaluating means (74) of an apparatus as claimed in claim 10 for carrying out the method of determining a spatial distribution of magnetic particles (102) in an examination zone with a first, time-constant magnetic field and a second, time-variable magnetic field, wherein the second, time-variable magnetic field has a fundamental frequency and an amplitude in each spatial component and the time derivative of the second magnetic field is substantially identical for each spatial component, or the second, time-variable magnetic field encompasses a sum of several second, time-variable partial magnetic fields, each partial magnetic field having a fundamental frequency and an amplitude in each spatial component and the time derivative of the second magnetic field and/or of the second partial magnetic fields being substantially identical for each spatial component.

\* \* \* \* \*